United States Patent [19]

Murphy

[11] 4,169,468
[45] Oct. 2, 1979

[54] MULTIPLE CAST POSITIONER DEVICE

[76] Inventor: Jack Murphy, 25361 Yale St., Hemet, Calif. 92343

[21] Appl. No.: 848,198

[22] Filed: Nov. 3, 1977

[51] Int. Cl.² .............................................. A61F 5/04
[52] U.S. Cl. ......................................... 128/83; 128/94
[58] Field of Search ............... 128/94, 90, 91 R, 84 R, 128/84 C, 83

[56] References Cited

U.S. PATENT DOCUMENTS

| D. 200,752 | 3/1965 | Hill | 128/94 X |
| 1,149,341 | 8/1915 | Carlson | 128/84 C |
| 2,696,208 | 12/1954 | Falls | 128/84 C |
| 2,750,939 | 6/1956 | Bolger | 128/84 R |
| 2,856,919 | 10/1958 | Murray | 128/90 |
| 4,023,568 | 5/1977 | Murphy | 128/94 |

*Primary Examiner*—John D. Yasko
*Attorney, Agent, or Firm*—John Joseph Hall

[57] ABSTRACT

A multiple cast positioner device which, upon being embedded in a cast of a person's limb, provides multiple traction loop members, each formed on top of a base member inserted in a longitudinal bracket, thereby permitting the use of traction systems adjustable as desired for care and manipulation of the person's limb.

5 Claims, 11 Drawing Figures

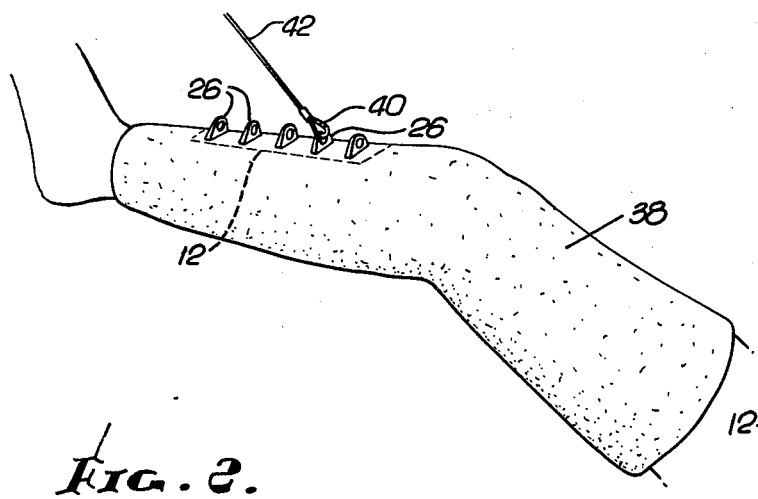
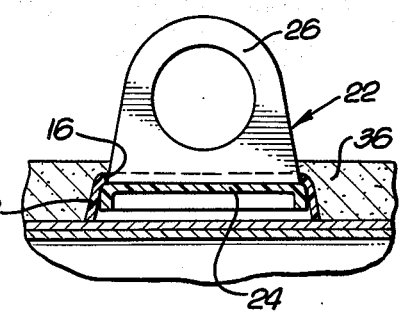
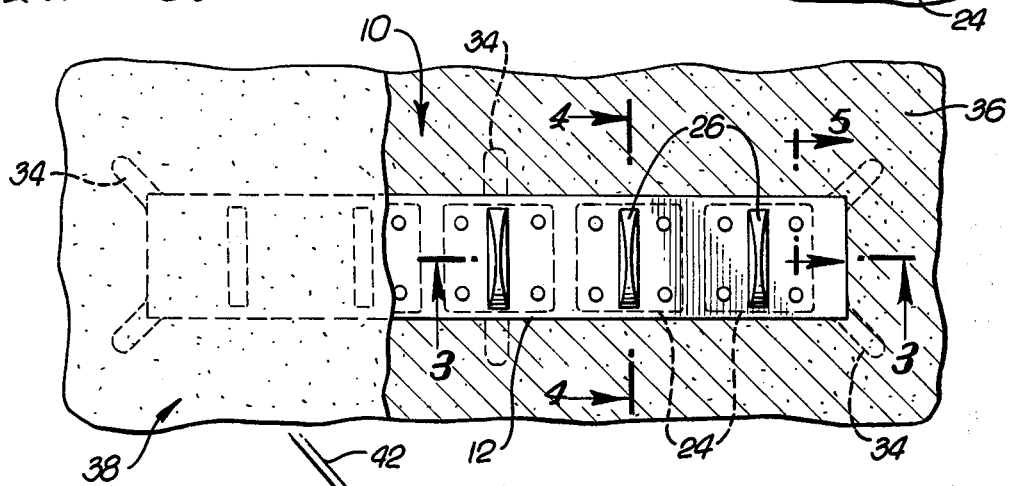
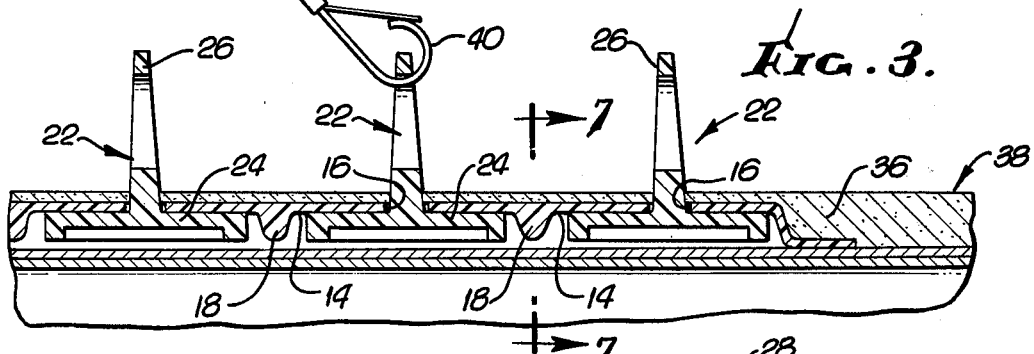
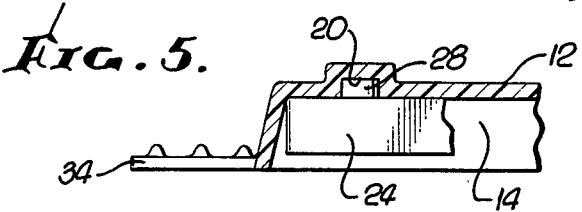
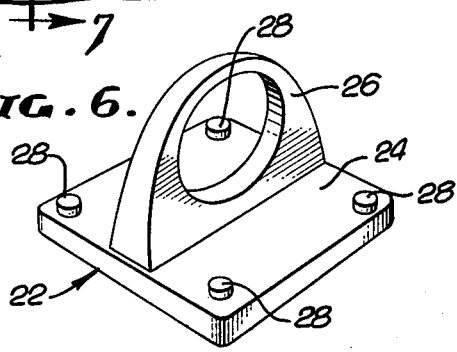

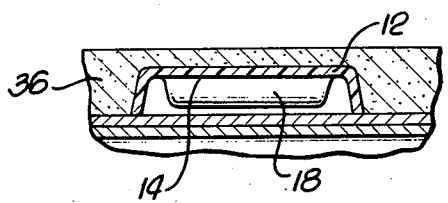
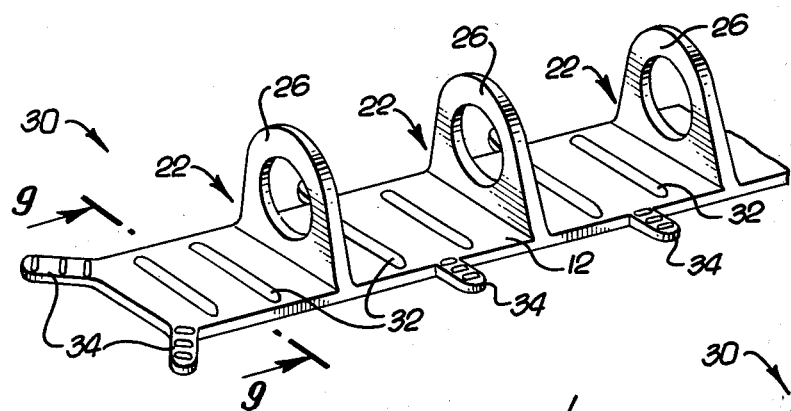
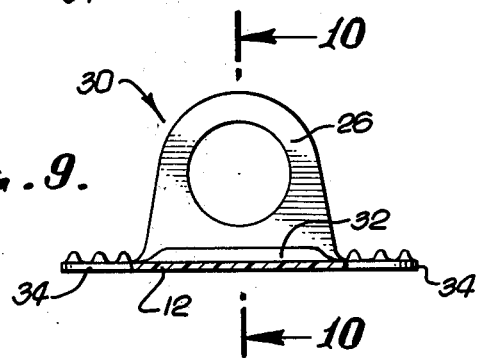
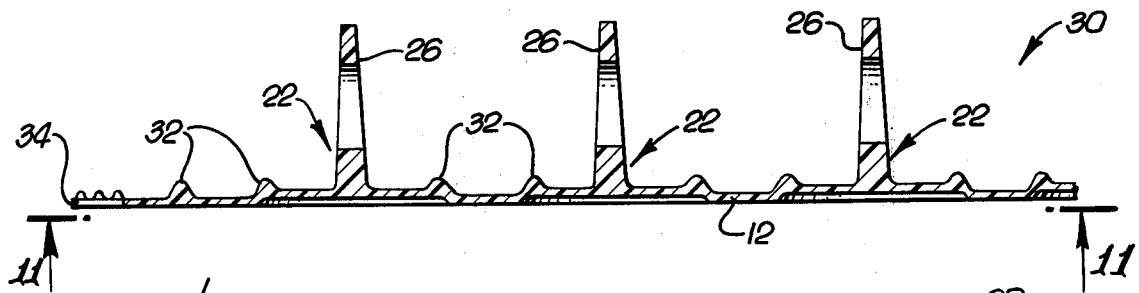
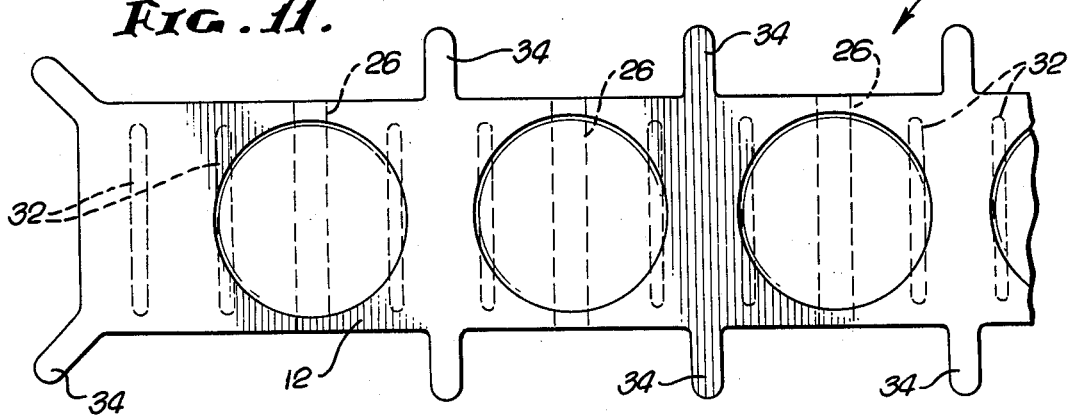

MULTIPLE CAST POSITIONER DEVICE

BACKGROUND OF THE INVENTION

This invention relates to the field of positioning devices for casts on a patient's limb which has the capability of being constantly adjusted as to position in conjunction with adjustable traction systems.

SUMMARY OF THE INVENTION

The multiple cast positioner device has a longitudinal bracket member with multiple slots, upper and lower, for receiving traction loop members having a rectangular base with a top portion formed into an eyelet. Upon being inserted into the slots, the traction loop members are snapped into position with pins at each corner fitting into recesses formed on the top portion of the bracket member.

Another embodiment of the invention comprises a longitudinal bracket member having a plurality of integrally formed and spaced eyelets on its top portion, with anchor members for securing purposes.

The invention provides a capability of rapidly and easily adjusting the position of a cast on a patient's limb as desired for fracture alignment maintenance and similar purposes, under traction.

It is, therefore, an object of this invention to provide a multiple cast positioner device for use in conjunction with adjustable traction systems.

Another object of the invention is to provide a multiple cast positioner device which permits rapid and easy adjustment in position of a cast on a patient's limb.

A further object of this invention is to provide a multiple cast positioner device which facilitates constant readjustment of position of a cast on a person's limb for fracture alignment maintenance.

A yet further object of this invention is to provide a multiple cast positioner device which is relatively easy to install and maintain in a cast for a patient's limb.

These and other objects will be more readily understood by reference to the accompanying claims and drawings, in which FIG. 1 is a perspective view of an embodiment of the invention in place, embedded in a cast around the limb of a person.

FIG. 2 is a top plan view of an embodiment of the invention.

FIG. 3 is a section taken along line 3—3 of FIG. 2.

FIG. 4 is a section taken along line 4—4 of FIG. 2.

FIG. 5 is a section taken along line 5—5 of FIG. 2.

FIG. 6 is a perspective view of a traction loop member.

FIG. 7 is a section taken along line 7—7 of FIG. 3.

FIG. 8 is a perspective view of another embodiment of the invention.

FIG. 9 is a section taken along line 9—9 of FIG. 8.

FIG. 10 is a section taken along line 10—10 of FIG. 9.

FIG. 11 is a section taken along line 11—11 of FIG. 10.

With respect to the drawings, FIGS. 1-7 show one embodiment 10 of the invention having a longitudinal bracket member 12 with a plurality of slots 14 in its base portion, and a plurality of face slots 16 in its top portion, separated by ribs 18. The top portion of bracket member 12 has a plurality of recesses 20 on each side.

Traction loop member 22 is formed with a rectangular base 24 having a top portion shaped into an eyelet 26. Each corner of the base 24 is provided with a pin member 28 for insertion into a recess 20 of bracket member 12.

Preferably, the base 24 is cored out from underneath to improve flexibility and equalize the stress points affecting base 24, thereby greatly reducing the possibility of cracking of the traction loop member 22.

Another embodiment 30 of the invention is illustrated in FIGS. 8-11, wherein a plurality of traction loop members 22 having eyelets 26 are formed integrally with bracket member 12, and are located parallel to each other and arranged at right angles to the longitudinal axis of bracket member 12. The bottom portion of traction loop members 22 is cored out for improved flexibility and equalization of stress points, to reduce the possibility of cracking. This embodiment 30 is optionally provided with ribs 32 and anchor members 34 for additional security when embedded in a cast. Anchor members 34 and ribs 32 may also be added optionally to embodiment 10 as desired by forming them on bracket member 12.

Any suitable material having the requisite strength and flexibility may be used to construct the invention. Radiolucent material is preferred.

In operation, the embodiment 10 of the multiple cast positioner device is prepared for embedding in plaster 36 while wet, by inserting the desired number of traction loop members 22 into slots 14 and 16, and snapping pins 28 into position in recesses 20.

Preferably, the traction loop members 22 are located parallel to each other and arranged at right angles to the longitudinal axis of bracket member 12. Both the number and location of traction loop members 22 inserted into bracket member 12 may be varied as desired by pre-selection before being embedded in plaster 36, thereby providing great flexibility of positions available for traction.

The assembled multiple cast positioner is then embedded in wet plaster 36 of a cast 38 for a patient's limb, so that bracket member 12 is below the surface of the plaster 36, and the eyelets 26 are projecting above the surface of cast 38, and capable of receiving a clip holder 40 attached to a cord 42. After the plaster 36 has dried, the cast 38 may then be connected to adjustable traction systems and the position of the cast 38 may be readily and constantly readjusted as desired by changing the location of clip holder 40 to a different eyelet 26. In this way, fracture alignment maintenance is achieved throughout the healing process by providing easy and rapid readjustment of the force vectors involved in dynamic traction systems.

The embodiment 30 of the invention is placed in operation in a similar manner as embodiment 10.

Although I have described my invention in detail with reference to the accompanying drawings illustrating preferred forms of my invention, it is understood that numerous changes in the details of construction and arrangement of parts may be made without departing from the spirit and scope of the invention as hereinafter claimed.

I claim:

1. A multiple cast positioner device for embedding in a cast of a patient's limb, comprising:

an elongated bracket member having a plurality of base slots and face slots, and with recesses in its top portion; and a traction loop member having a base with its top portion having a pin member at each corner and an eyelet, said traction loop member being insertable into one of said base slots and one of said face slots of said elongated bracket member.

2. A multiple cast positioner device according to claim 1 in which said traction loop member has a rectangular base.

3. A multiple cast positioner device according to claim 1 in which said elongated bracket member is provided with a plurality of anchor members for additional security when embedded.

4. A multiple cast positioner device according to claim 1 in which said traction loop member is inserted into one of said base slots and one of said face slots of said elongated bracket member and arranged with said eyelets of said traction loop member at right angles to the longitudinal axis of said bracket member.

5. A multiple cast positioner device according to claim 2 in which said bracket member has a plurality of anchor members for additional security when embedded.

* * * * *